United States Patent
Wang

(10) Patent No.: US 10,617,505 B2
(45) Date of Patent: Apr. 14, 2020

(54) CONDUCTIVE AND DEGRADABLE IMPLANT FOR PELVIC TISSUE TREATMENT

(71) Applicant: Boston Scientific Scimed, Inc., Maple Grove, MN (US)

(72) Inventor: Guangjian Wang, Falcon Heights, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 375 days.

(21) Appl. No.: 14/432,390

(22) PCT Filed: Oct. 1, 2013

(86) PCT No.: PCT/US2013/062870
§ 371 (c)(1),
(2) Date: Mar. 30, 2015

(87) PCT Pub. No.: WO2014/055521
PCT Pub. Date: Apr. 10, 2014

(65) Prior Publication Data
US 2015/0238300 A1 Aug. 27, 2015

Related U.S. Application Data

(60) Provisional application No. 61/708,434, filed on Oct. 1, 2012.

(51) Int. Cl.
*A61F 2/02* (2006.01)
*A61F 2/00* (2006.01)
(Continued)

(52) U.S. Cl.
CPC .......... *A61F 2/0063* (2013.01); *A61F 2/0045* (2013.01); *A61L 31/06* (2013.01);
(Continued)

(58) Field of Classification Search
CPC ............... A61F 2/0063; A61F 2/0045; A61F 2002/0068; A61F 2002/0072; A61F 2210/0004; A61F 2250/0001
See application file for complete search history.

(56) References Cited

U.S. PATENT DOCUMENTS 2,671,444 A * 3/1954 Pease, Jr. .............. A61F 2/0063
606/151
3,531,561 A 9/1970 Trehu
(Continued)

FOREIGN PATENT DOCUMENTS

| EP | 1 466 934 | 10/2004 |
| WO | 9716545 A1 | 5/1997 |

(Continued)

OTHER PUBLICATIONS

Rajesh, et at. "Conducting polymeric nanotubules as high performance methanol oxidation catalyst support" Chem. Comm. (2003) pp. 2022-2023.

(Continued)

*Primary Examiner* — Katherine M Rodjom
(74) *Attorney, Agent, or Firm* — Brake Hughes Bellermann LLP

(57) ABSTRACT

Described is a pelvic implant comprising a biodegradable conductive mesh. The mesh can include biodegradable and electrically conductive polymer, and can be stimulated with a current to generate an electric field to promote an improved tissue response following placement of the implant. The invention also describes methods and systems including the pelvic implant comprising a biodegradable conductive mesh for the treatment of pelvic floor conditions. Implants of the invention provide benefits relating to improved tissue integration into the mesh, resulting in pelvic tissue reconstruc- (Continued)

tion. Tissue reconstruction and elimination of the mesh materials can lead to a better clinical outcome for the patient.

17 Claims, 4 Drawing Sheets

(51) Int. Cl.
    *A61L 31/14*     (2006.01)
    *A61N 1/05*     (2006.01)
    *A61L 31/10*     (2006.01)
    *A61L 31/06*     (2006.01)
    *A61N 1/36*     (2006.01)

(52) U.S. Cl.
    CPC ............... *A61L 31/10* (2013.01); *A61L 31/14* (2013.01); *A61L 31/148* (2013.01); *A61N 1/0514* (2013.01); *A61F 2210/0004* (2013.01); *A61F 2250/0001* (2013.01); *A61N 1/36007* (2013.01)

(56) References Cited

U.S. PATENT DOCUMENTS

| | | | |
|---|---|---|---|
| 4,696,835 A | 9/1987 | Maus et al. | |
| 5,069,820 A | 12/1991 | Jen et al. | |
| 5,069,821 A | 12/1991 | Jen et al. | |
| 5,211,810 A | 5/1993 | Bartholomew et al. | |
| 6,669,706 B2 * | 12/2003 | Schmitt | A61F 2/0063 606/151 |
| 7,070,556 B2 | 7/2006 | Anderson et al. | |
| 7,070,610 B2 * | 7/2006 | Im | A61B 17/06166 606/230 |
| 7,351,197 B2 | 4/2008 | Montpetit et al. | |
| 7,422,557 B2 | 9/2008 | Arnal et al. | |
| 7,500,945 B2 | 3/2009 | Cox et al. | |
| 7,722,528 B2 | 5/2010 | Arnal et al. | |
| 7,740,576 B2 | 6/2010 | Hodroff et al. | |
| 7,901,346 B2 | 3/2011 | Kovac et al. | |
| 7,905,825 B2 | 3/2011 | Arnal et al. | |
| 7,914,437 B2 | 3/2011 | Gozzi et al. | |
| 8,084,111 B2 | 12/2011 | Wu | |
| 2005/0096499 A1 * | 5/2005 | Li | A61F 2/0045 600/37 |
| 2006/0195007 A1 | 8/2006 | Anderson et al. | |
| 2007/0185541 A1 * | 8/2007 | DiUbaldi | A61N 1/0512 607/41 |
| 2007/0219606 A1 * | 9/2007 | Moreci | A61B 18/1492 607/101 |
| 2010/0076254 A1 | 3/2010 | Jimenez et al. | |
| 2013/0131830 A1 * | 5/2013 | Lelkes | A61L 27/26 623/23.72 |
| 2013/0204078 A1 * | 8/2013 | Li | A61F 2/0063 600/37 |

FOREIGN PATENT DOCUMENTS

| | | |
|---|---|---|
| WO | WO 2007/016083 | 2/2007 |
| WO | 2007106520 A2 | 9/2007 |
| WO | 2008016802 A1 | 2/2008 |
| WO | WO 2011/063412 | 5/2011 |
| WO | WO 2011/072148 | 6/2011 |
| WO | WO 2011/143572 | 11/2011 |
| WO | WO 2012/116182 | 8/2012 |

OTHER PUBLICATIONS

Menon, et al. "Investigation of Molecular and Supermolecular Structure in Template-Synthesized Polypyrrole Tubules and Fibrils" Chem. Mater. 8, (1996) pp. 2382-2390.
Bjorklund, et al. "Some Properties of Polypryyole-Paper Composites" J. Electron. Mat., vol. 13, No. 1, (1984) pp. 211-230.
Paul, et al., "Melt/Solution Processable Polyaniline with Functionalized Phosphate Ester Dopants and its Thermoplastic Blends" Journal of Applied Polymer Science, vol. 80, (2001), pp. 1354-1367.
First Examination Report for Australian Application No. 2013327478, dated Apr. 28, 2017, 4 pages.
Response to First Examiner's Report for Australian Application No. 2013327478, filed Mar. 15, 2018, 13 pages.
Second Examiner's Report for Australian Application No. 2013327478, dated Mar. 23, 2018, 3 pages.

* cited by examiner

CONDUCTIVE AND DEGRADABLE IMPLANT FOR PELVIC TISSUE TREATMENT

PRIORITY CLAIM

This application claims the benefit from International Application No. PCT/US2013/062870, filed Oct. 1, 2013, which in turn claims priority under 35 USC § 119(e) from U.S. Provisional Patent Application Ser. No. 61/708,434, filed Oct. 1, 2012, entitled CONDUCTIVE AND DEGRADABLE IMPLANT FOR PELVIC TISSUE TREATMENT, both of which are incorporated herein by reference in their entireties.

FIELD OF THE INVENTION

The present invention relates generally to surgical methods and apparatus and, more specifically, to surgically implantable mesh that are electrically conductive and biodegradable.

BACKGROUND OF THE INVENTION

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

Urinary incontinence can be characterized by the loss or diminution in the ability to maintain the urethral sphincter closed as the bladder fills with urine. Male or female stress urinary incontinence (SUI) generally occurs when the patient is physically stressed.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

The inventors of the current technology of the application have discovered that there is a need to provide an effective implantable biodegradable mesh that has an improved tissue healing function, that is non-permanent, and that can be used to treat pelvic tissue problems such as incontinence, and/or pelvic organ prolapse and other conditions. According to the current application, the inventors provide new electrically conductive and biodegradable mesh implants for correcting pelvic tissue disorders and improving healing of pelvic tissue following implantation.

SUMMARY OF THE INVENTION

The present invention describes electrically conductive and biodegradable pelvic mesh implants and methods for treating pelvic conditions. Exemplary conditions include those such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness.

In one embodiment the invention provides an implant configured for the placement at a pelvic floor tissue, the implant comprising electrically conductive and biodegradable mesh. The entire mesh or part of the mesh can be conductive. The mesh can be in the form of an elongate sling, strip, or mesh tape, or can be a central support having non-elongate shape. In exemplary constructions the mesh comprises an electrically conductive polymer coated on the surface of a biodegradable elongate structural feature of a mesh, such as a biodegradable filament, or a strut of a biodegradable molded mesh. In other exemplary constructions the mesh comprises an electrically conductive polymer incorporated into a biodegradable elongate structural feature of a mesh.

Another embodiment of the invention provides a system for the treatment of pelvic floor tissues. The system comprises an implant configured for the placement at a pelvic floor tissue, the implant comprising an electrically conductive and biodegradable mesh, and an electrical stimulator unit capable of generating a current through the mesh. In embodiments, the electrical stimulator can be implantable or non-implantable, and stimulation can be carried out internally or transcutaneously. Optionally included in the system are one or more tools for the introduction of the implant into pelvic tissue, such as needle introducers which can guide the implant to target areas in the pelvic tissue. Optionally included in the system are tissue anchors which can help fix the implant in a desired pelvic tissue location.

Yet another embodiment of the invention provides a method for the treatment of pelvic floor tissues. The method comprises steps of (a) placing an implant at a pelvic floor tissue, the implant comprising an electrically conductive and biodegradable mesh; (b) generating a current through the mesh to promote a tissue healing response; and (c) allowing the biodegradable mesh to degrade at the site of placement.

The electrically conductive and biodegradable mesh, and associated system and method can provide advantageous benefits in this field of technology. For example, since the mesh is electrically conductive a current (e.g., DC) can be safely applied to the mesh shortly after surgical implantation and recovery. This current can create a therapeutic electric field around the mesh in surrounding tissues and facilitate tissue healing in association with the mesh and surrounding tissues through one or more physiological mechanism(s) such as electrotaxis, cytokine secretion, mitochondrial function, cellular adhesion, spreading, and proliferation. The electrical stimulation can promote healthy tissue growth into the mesh and enhance healing of the tissue in the surgical area. The implant and method of the invention can reduce the risk of future tissue complication and strengthen tissue attachment to the mesh to provide a better mechanical support. Further, the mesh provides scaffolding or guidance for the reconstruction of tissue to provide a level of support greater than the support found prior to implantation.

The mesh is also biodegradable, and its rate of degradation in vivo can be controlled by the type and amount of biodegradable material (e.g., type and percentage of biodegradable polymer) in the mesh. The rate of degradation can coincide with the establishment and reconfiguration of supporting pelvic structures/tissues in vivo. For example, the mesh can degrade and be absorbed in vivo when the pelvic tissue is healed and mechanical features of the mesh are no longer needed for supporting for pelvic tissue.

DETAILED DESCRIPTION

Figure 1:
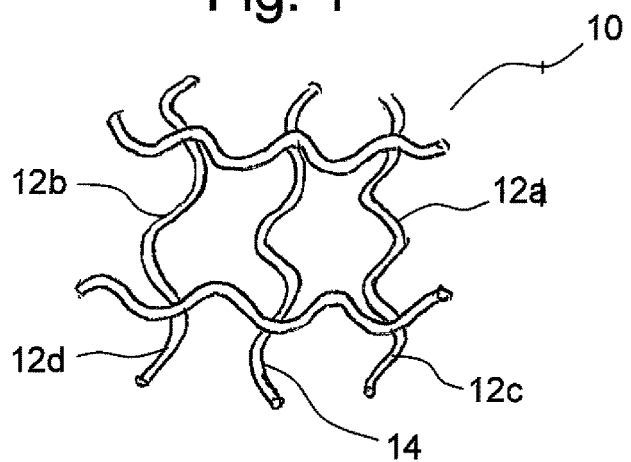
FIG. 1 is an illustration of a portion of a biodegradable conductive mesh with biodegradable and conductive monofilaments.

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

Generally the mesh implants of the invention have conductive and biodegradable features, and are configured for implantation in a pelvic area in a patient. The mesh of the invention can be used for supporting tissue in an area of treatment. For a period of time before it degrades, the mesh can provide physical support to the tissue to help treat the pelvic tissue disorder. During this period, the mesh supports weakened tissue while electrical current is provided through the mesh. The electrical current causes cells involved in a wound healing response to migrate to the area of the implanted mesh, where the cells can associate directly with the mesh or localize to the mesh area. The mesh structure can be used as a scaffold on which new tissue is formed and that begins to replace the support function of the mesh. The electrical current can also provide stimulation for cellular activity such as nerve regeneration and muscle regeneration. Over a period of time, the mesh material degrades but leaves in place the new tissue formed by the cells attracted to the mesh area through the electrical stimulation. The conductive material of the mesh can be dissolved or absorbed as the degradable material of the mesh is eroded at the implantation site.

The term "mesh" refers to a material construction having openings ("apertures") that is capable of supporting a tissue for a period of time and allowing cell in-growth. Within the context of use as a pelvic implant, meshes of the invention are not limited to any particular construction, shape, or size, although certain detailed embodiments are described herein to illustrate concepts of the invention. In some cases, the mesh can be of a "woven" construction made from monofilaments, multifilaments, yarns of degradable material, and the like. In other cases, the mesh can be of a "non-woven" construction made from a molded degradable material.

The mesh, in either woven or non-woven molded form, can have an "elongate structural feature," which refers to, for example, all or a portion of a monofilament of a woven mesh (e.g., feature 12a in FIG. 1), or a "strut" of a portion of a non-woven molded mesh.

The biodegradable mesh material can be made from a single biodegradable material or a combination of biodegradable materials. In some embodiments the implant has a knitted or woven construction using monofilaments formed of a biodegradable material, or combination of biodegradable materials.

Biodegradable materials include, but are not limited to, biodegradable homopolymers, biodegradable copolymers, and blends of biodegradable polymers. Degradation of the mesh can occur by using a mesh made from a polymer that has hydrolytically unstable linkages in the backbone. Common hydrolytically unstable chemical groups of biodegradable polymers in vivo include esters, anhydrides, orthoesters, and amides.

Biodegradable homopolymers and copolymers can be formed from monomers such as glycolide, lactide, and stereoisomers thereof, ε-caprolactone, valerolactone, hydroxybutyric acid, hydroxypentanoic acid, trimethylene carbonate, and dioxanone. Exemplary biodegradable polymers include polyhydroxyalkanoates (e.g., poly-4-hydroxybutyrate (P4HB), poly(3-hydroxyvalerate), and poly(hydroxybutyrate-co-hydroxyvalerate)); polyesters (e.g., poly (L-lactide) (LPLA); poly(DL-lactide) (DLPLA); poly(L-lactide-co-glycolide) (LPLG); poly(DL-lactide-co-L-lactide) (LDLPLA); poly(glycolide-co-trimethylene carbonate) (PGA-TMC); poly(DL-lactide-co-glycolide) (DLPLG); poly(ε-caprolactone) (PCL); poly(valerolactone); poly(glycolic acid); poly(glycolide) (PGA); and poly(dioxanone) (PDO)); polyorthoesters; polyalkeneanhydrides, e.g., poly(sebacic acid); polyanhydrides, and polyphosphazine.

The biodegradable polymers may be described with reference to chemical and physical properties of the polymers. For example, the biodegradable polymer may be described with reference to properties such as melting point, glass transition temperature, modulus (tensile or flexural), elongation, and degradation time (e.g., in vivo).

For example, for some degradable polymers melting point can be in the range of about 50-250° C. PCL has a melting point of about 58-63° C.; LPLA has a melting point of about 173-178° C.; and PGA has a melting point of about 225-230° C. Some degradable polymers can be classified as amorphous. Degradable polymers can have glass transition temperatures in certain ranges, such as from about 30-70° C.; 35-40° C. (e.g., PGA); 60-65° C. (e.g., LPLA); 55-60° C. (e.g., DLPLA); 45-55° C. (e.g., DLPLG copolymers). Degradable polymers can have moduli (tensile or flexural) in the range of about 0.4-8 Gpa, about 0.5-3 Gpa, about 1-2.5 Gpa, about 1.5-2.5 Gpa, about 2-2.5 Gpa, about 6-8 Gpa, or about 7-8 Gpa. Degradable polymers can have elongation in the range of about 1-500%, 3-10% (e.g., DLPLA), 5-10% (e.g., LPLA), 15-20% (e.g., PGA), or 300-500% (e.g., PCL).

Monofilaments formed of a biodegradable polymer can be prepared by methods known in the art. An exemplary process for filament formation includes polymer melting, extrusion, quenching, and drawing. Polylactide polymers, for example, can be melt extruded from a die at a temperature in the range of about 185° C. to 215° C., and the extrudate quenched at about room temperature. The extruded material can be drawn from the die in the presence of a suitable liquid at a desired ratio. Draw ratio, drawing rate, and drawing temperature can affect physical characteristics of the formed monofilament. See, for example, U.S. Pat. No. 3,531,561. Conductive material can be included in the extruded composition or applied to a surface of the monofilament after it is extruded.

Monofilaments made from two different biodegradable polymers can be used. For example, biodegradable polymers having two different moduli can be co-extruded to form monofilamens. Exemplary combinations include polydioxanone/polycaprolactone, poly(glycolic acid-co-caprolactone)/polycaprolactone, polydioxanone/poly(lactide-co-caprolactone); and polydioxanone/polycaprolactone. See, for example, U.S. Pat. No. 7,070,610.

In other modes of practice, monofilaments can be prepared by extruding the biodegradable polymer in the form of a sheet and then mechanically processing the extruded sheet, such as by laser cutting, into monofilaments.

Exemplary monofilaments have diameters in the range of about 10 μm to about 250 μm (~0.0004 to ~0.01 inches), or more specifically from about 25 μm to about 150 μm (~0.001 to ~0.006 inches). The monofilaments may also be described with regards to cross sectional area, which can be determined. In some aspects, the monofilaments have a cross sectional area in the range of about 75 μm$^2$ to about 0.05 mm$^2$, or more specifically in the range of about 490 μm$^2$ to about 0.0175 mm$^2$. The monofilament size can be described with or without the conductive material. In some cases, if the conductive material is included, such as incorporated or formed as a coating on the monofilament, this can increase the diameter of the monofilament.

Figure 6:
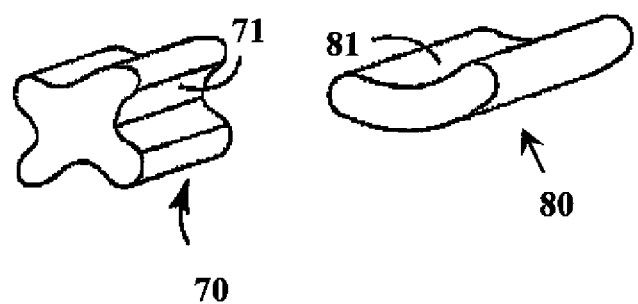
FIG. 6 is an illustration of a monofilament with grooves.

The shape of a cross section of the monofilament can be substantially circular, oval, or can be of other curved or non-curved shapes. For example, the shape of a cross section of the monofilament can be polygonal, such as square, rectangular, hexagonal, or octagonal, etc. In some configurations the monofilament can have grooves which can effectively increase the amount of surface area of the monofilaments. For example, with reference to FIG. 6, the monofilament (70 or 80) can have a shape that forms one or more grooves along the length of the monofilament (e.g., 71 or 81). In some embodiments, one or more of the grooves of the monofilament can be filled with a conductive polymeric material.

In other constructions the conductive biodegradable mesh implant includes a non-knitted/non-woven (e.g., molded) polymeric mesh. Molded meshes can be formed of patterned cells by way of a molding, die casting, laser etching, laser cutting, extruding, punching, or 3-D printing process. The portion of the implant that is the molded mesh can be considered a homogenous unitary construct. The molded mesh can be constructed of a absorbable polymer material to provide a lattice support structure of repeated apertures or cells. Repeated apertures in the implant generally form a lattice structure and can be cut or molded into sinusoid, or other waveform or undulating strut patterns to control elongation or compression along single or multiple axes to define a desirable pattern density with overall reduced surface area, and to control the distribution and shaping from applied loads. Various techniques can be used to make a non-woven polymeric mesh. Molded polymeric meshes are described in, for example, commonly assigned PCT Publication Nos. WO2011/063412 and WO2011/072148, which describes molded meshes that can be made from bioabsorbable polymers such as PGA and PLA.

The size and shape of the openings in the mesh can be defined by the weave or knitting patterns of the woven mesh, or the molding pattern of the non-woven mesh. The openings can be of any one or combination of shapes, such as square, rectangular, triangular, oval, circular, or more complex polygonal shapes (hexagonal, etc.), as well as irregular shapes, such as might be associated with more complex knitted or woven constructs.

Exemplary sizes of the apertures in the mesh construct can be in the range of about 0.2 mm$^2$ to about 2 mm$^2$, or more specifically in the range of about 0.5 mm$^2$ to about 1.5 mm$^2$. A complex knitted, woven, or molded construct may have apertures of various sizes.

In some aspects the thickness of the degradable mesh is in the range from about 0.004 inches (~0.1 mm) to about 0.020 inches (~0.58 mm).

In some cases the mesh can also be defined in terms of its basis weight. In many constructions a mesh with a lower basis weight can be more porous or have larger openings, whereas a mesh with a higher basis weight is less porous or has smaller openings. In some aspects the mesh has a basis weight in the range of 5 g/m$^2$ to about 100 g/m$^2$, and more specifically in the range of 10 g/m$^2$ to about 50 g/m$^2$, or about 15 g/m$^2$ to about 30 g/m$^2$.

Mesh porosity can be expressed in terms of percent porosity. "Porosity" refers to the percentage of the area (flat surface) of the mesh that has openings. In some aspects, the mesh has porosity of greater than 50%, or more specifically greater than 60%, 70%, or 75%.

The mesh of the implant can be prepared to provide a desired degree of flexibility or rigidity suitable for the surgical implantation and treatment of target tissue. In some preferred constructions the mesh of the implant has a degree of rigidity to prevent it from buckling when in contact with pelvic tissue. Flexibility can be measured in gram-force-cm$^2$/cm$^2$.

In some aspects, the biodegradable conductive mesh comprises a conductive polymer. A conductive polymer can be associated with a portion of the mesh in one or more of a variety of ways so an electric field-generating current can be carried through all or a portion of the mesh. For example, in some cases the mesh comprises at least two different filaments, with one filament type comprising a conductive polymer. In other cases the mesh comprises a mixture of a conductive and a biodegradable polymer. In other cases the mesh comprises a conductive polymer coated on a biodegradable polymer. At least one of the fibers or struts of the mesh that is conductive can be attached, directly or indirectly, to cathode and anode of a power supply.

Conductivity values can be used to describe conductive features of the mesh. For example, a feature of the polymeric mesh, such as a fiber or strut, can be described in terms of SI units of conductivity described as siemens per meter (S/m) or siemens per centimeter (S/cm). For example, a conductive feature of the mesh may have a conductivity of 0.1 S/cm or greater, 1 S/cm or greater, 10 S/cm or greater, 100 S/cm or greater. Comparatively, a poorly conductive or non-conductive mesh feature may be described as having a conductivity of 0.01 S/cm or less, 0.001 S/cm or less, 0.0001 S/cm or less, or 0.00001 S/cm or less, or 0.000001 S/cm or less.

Exemplary conductive polymers can include, but are not limited to poly(pyrrole), polythiophenes, poly(3,4-ethylenedioxythiophene) (PEDOT), polyanilines, polyacetylenes, and polymer blends thereof.

Conductive polymers generally have a conjugated pi-bonded backbone with the ability to delocalize electrons, and also have counter ions for electroconductivity. Mobile carriers can be introduced into the double bonds by a doping process (such as oxidation or reduction reactions) in order to make the polymers electrically conducting. Doping can be more specifically p-doping or n-doping relative to the positive or negative sign of the injected charge in the polymer chain. These charges remain delocalized being neutralized by the incorporation of counter-ions (anions or cations). Exemplary conterions (also referred to as "dopants" or "ionic electrolytes") include but are not limited to: poly (styrene sulfonate), $LiCIO_4$, Phosphate-buffered saline (PBS), Hank's Balanced Salt Solution (HBSS), Collagen, Poly-D-Lysine (PDL), Poly-L-Lysine, poly-ornithine, poly acrylic acid, dodecylbenzene sulfonic acid (DBSA), p-toluenesulfonic acid (p-TSA), heparin, ferric fluoride, and combinations thereof.

Polypyrrole fibers of tubules can be prepared and used in the preparation of a biodegradable mesh construct. Polypyrrole fibers can be prepared by chemical or electrochemical processing involving growth within a pore or by using surfactant mediation. Pore templated growth of PPy tubes can be performed by polymerization within the pores of porous alumina and polycarbonate membranes (see, e.g., Rajesh, B., et at. (2003) *Chem. Comm.* 2022; and Menon, V. P., et al. (1996) *Chem. Mater.* 1996, 8, 2382) The membrane can be selectively dissolved to provide the PPy tubules.

In one mode of practice, polypyrrole is deposited a biodegradable mesh material such a biodegradable fiber or a biodegradable molded material. For example, a biodegradable mesh material such as PLLA fibers is first placed in ferric chloride solution prior to before immersion in a pyrrole solution. (e.g., see Bjorklund, R. B.; Lundstroem, I. (1984) *J. Electron. Mat.*, 13, 211.) In another mode of practice ferric chloride is exposed to the pyrrole monomer in the vapor phase (e.g., see U.S. Pat. No. 4,696,835). Solvents such as methanol can be used to prepare a coating composition.

The coating process may also use additives or include treatment steps to enhance coating formation. For example, a hydrophobic surfactants such as alkylnaphthyl-sulfonate can be used to promote formation of the coating. Poly (vinyl alcohol) can also be used as a surfactant to improve PPy coating a degradable materials In another mode of practice, a coating of conductive polymer can be formed on the degradable material by in-situ polymerization (e.g., see U.S. Pat. No. 5,211,810). Monomer material can absorb on the degradable material surface and polymerize to form a smooth continuous film.

In other embodiments, the conductive polymer is polyaniline. Aniline polymers include those that are soluble in organic solvents as well as those that are water soluble. Analine polymers are commercially available, such as from Panipol Oy, Finland, for example, PANIPOL™ F.

An exemplary polyaniline polymer is as described in EP1466934 B1:

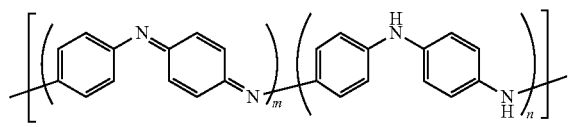

wherein m and n are molar fractions of a quinonediimine structural unit and a phenylenediamine structural unit in the repeating unit, respectively, and wherein: $0 \leq m \leq 1$, $0 \leq n \leq 1$ and $m+n=1$. Such a polymer can be prepared by the oxidation polymerization of aniline.

Other exemplary polyaniline polymers are described in U.S. Pat. No. 8,084,111, with a polyaniline dialkylsulfate complex shown below:

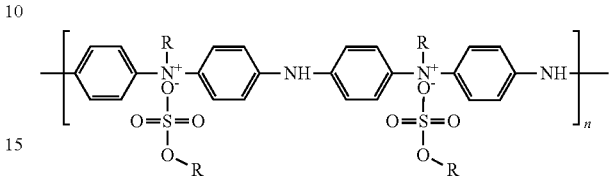

wherein n is the degree of polymerization of from about 30 to about 300, or from about 50 to about 100; and R is alkyl having from about 1 to about 18 carbon atoms. Such a polymer can be prepared by mixing PANIPOL® F, emeraldine salt (Panipol Oy; Porvoo Finland), with dimethylsulfate in distilled water.

Other exemplary polyaniline polymers are described in U.S. Pat. No. 5,069,820:

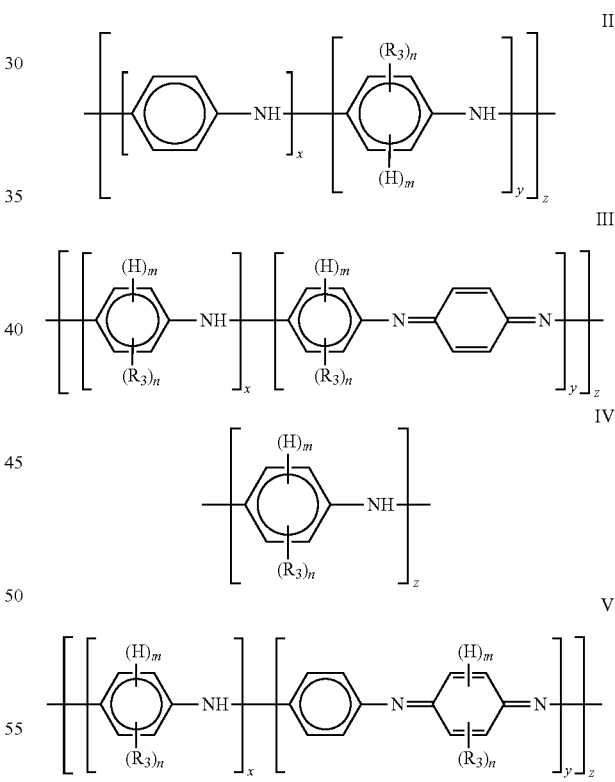

In Formulas II to V of U.S. Pat. No. 5,069,820, R2 and R4 are the same or different and are hydrogen or alkyl of 1-10 carbon atoms; R3 is the same or different and is selected from alkyl, alkenyl, alkoxy, cycloalkoxy, cycloalkenyl, alkanoyl, alkylthio; alkylamino, aryloxy, alkylthioalkyl, alkylaryl, arylalkyl, amino, dialkylamino, aryl, aryloxyalkyl, alkylsulfinylalkyl, alkylsulfonyl, arylsulfonyl, carboxylic acid, halogen, cyano, sulfonic acid, nitro, alkylsilane, or alkyl substituted with one or more of sulfonic acid, carboxylic acid, halo, nitro, cyano, or epoxy moieties; or any two R3 groups taken together may form an alkylene or alkylene chain completing a 3, 4, 5, 6, or 7-membered aromatic or acyclic ring that may include one or more divalent nitrogen, sulfur, sulfinyl, ester, carbonyl, sulfonyl, or oxygen atoms; soluble coating composition for application to the surface of a biodegradable mesh material.

In other embodiments, the polyaniline is water-soluble. Exemplary water-soluble polyaniline derivatives which are also self-acid-doped are described in Formula I of EP1466934 B1:

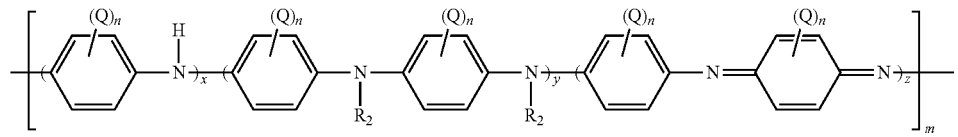

R3 is an aliphatic moiety having repeat units of either of the formula: $-(OCH_2CH_2)_qO-$ or $-(OCH_2CH(CH_3))_qO-$ wherein q is a positive whole number; y is an integer equal to or greater than 0; x is an integer equal to or greater than about 2, with the proviso that the ratio of x to y is greater than or equal to about 2; and z is an integer equal to or greater than 1.

In some aspects the polyaniline uses an acid dopant, such as one selected from anions of sulfonic acids (e.g., toluenesulfonic acid, dodecylbenzene sulfonic acid, camphor sulfonic acid, allylsulfonic acid, 1-propanesulfonic acid, 1-butananesulfonic acid, 1-hexanesulfonic acid, 1-heptanesulfonic acid, benzenesulfonic acid, styrenesulfonic acid, naphthalenesulfonic acid), and carboxylic acids (e.g., acetic acid and oxalic acid).

In some embodiments, the polyaniline uses dopants that also acts as a plasticizing cum protonating agent (see, for example, Paul, R. K. and Pillai C. K. S. (2001) Journal of Applied Polymer Science, 80:1354-1367). Examples of plasticizing dopants include 3-pentadecylphenyl-phosphoric acid (PDPPA), pentadecylphenyl(bis)phosphoric acid [PDP(bis)PA], monocardanylphosphoric acid (MCPA), dicardanylphosphoric acid (DCPA), and phosphorylated cashew nut shell liquid prepolymer (PCNSL).

The polyaniline polymers can be used to form the biodegradable mesh using solution processing or thermal processing techniques.

In some modes of practice the polyaniline is dissolved in a solvent, or combination of solvents to form a composition and the composition is used to provide a conductive feature in forming the mesh. For example, the composition can be a coating composition applied to a fiber or strut part of a mesh construct. Exemplary solvents for polyanilines include toluene, xylene, NMP, bicyclic terpenes, and methanol.

Exemplary coating composition use an concentration of polyaniline in the range of about 0.5 to about 10% (w/v). The concentration can be adjusted to control the layer resistivity as well as viscosity.

In other modes of practice the polyaniline is melt processed provide a conductive feature in forming the mesh. For example, the polyaniline can be melt extruded to form a fiber, and the fiber included in a mesh made from one or more other biodegradable fibers such as LPLA, DLPLA, LPLG, LDLPLA, PGA-TMC, DLPLG, PCL, or PGA. As another example, a mixture of polyaniline and a biodegradable polymer such as LPLA, DLPLA, LPLG, LDLPLA, PGA-TMC, DLPLG, PCL, or PGA are melt processed to form a fiber, or are molded into a mesh.

Water soluble polyalilines can be blended with biodegradable polymers having water solubility to provide compositions for preparing meshes, or can be prepared as a water wherein m is a natural number; n is a positive integer of from 1 to 4; x, y or z is 0 or 1 independently in each of the m pieces of substructures of Formula (I); x, y and z are not 0 simultaneously in each of the m pieces of substructures, y is 1 in at least one of the m pieces of substructures; Q is an atom or a functional group selected from a group consisting of fluorine, chlorine, bromine, $-OR_1$, $-COR_1$, $-OCOR_1$, $-NHCOR_1$, $-NO_2$, $-COOR_1$, $-CN$ and $-COOH$; wherein $R_1$ is a $C_1$-$C_4$ alkyl group, $R_2$ is a functional group expressed by Formula (II):

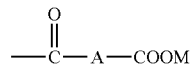

A is a substituted or unsubstituted $C_1$-$C_4$ alkylidene group, and wherein M is an atom or a functional group selected from a group consisting of hydrogen, lithium, sodium, potassium and $NH_4^+$.

In one exemplary construction, as shown in FIG. 1, the biodegradable conductive implant comprises a mesh made from at least two different fibers, one being a biodegradable fiber and another a conductive fiber. For example, a portion of biodegradable conductive mesh implant 10 is shown having biodegradable fibers 12a-12d and conductive fiber 14. The biodegradable fibers can comprise the majority of the amount of the fibers in the mesh, such as greater than 50% (wt), 60% (wt) or greater, 70% (wt) or greater, 80% (wt) or greater, 90% (wt) or greater, 95% (wt) or greater, or 97.5% (wt) or greater. In some cases the biodegradable fibers can be made from a biodegradable polymer selected from LPLA, DLPLA, LPLG, LDLPLA, PGA-TMC, DLPLG, PCL, PGA, or mixtures thereof. In embodiments wherein the biodegradable fiber is made entirely of a biodegradable polyester, the fiber may have no substantial conductivity.

The conductive fibers can comprise a minority of the amount of the fibers in the mesh, such as less than 50% (wt), 40% (wt) or less, 30% (wt) or less, 20% (wt) or less, 10% (wt) or less, 5% (wt) or less, or 2.5% (wt) or less. The conductive fiber can be made from a conductive polymer selected from poly(pyrrole), polythiophenes, poly(3,4-ethylenedioxythiophene) (PEDOT), polyanilines, or polyacetylenes. Optionally, the conductive fiber can include a biodegradable polymer selected from LPLA, DLPLA, LPLG, LDLPLA, PGA-TMC, DLPLG, PCL, PGA, or mixtures thereof. As such, and in some embodiments, the mesh can be made from a majority of biodegradable substantially non-conductive fibers, and a minority of biodegradable conductive fibers.

In yet other constructions, the mesh is prepared predominantly or entirely from conductive biodegradable fibers such as those having a mixture of a conductive polymer and a biodegradable polymer. For example, in some modes of preparation, the conductive polymer and the biodegradable polymer are both melt processable polymers that can blend upon heating, and the polymer blend can then be extruded or shaped into a monofilament, or the melted blend can be used to form a mesh structure in a molding process.

In one embodiment, the mesh comprises a polypyrrole (PPy) as a conductive polymer and poly (L-Lactide) (PLLA) as a biodegradable polymer. In some embodiments, the mesh has about 5% PPy and 95% PLLA. In some embodiments, the mesh has about 5% polyaniline and 95% PLLA. The amounts of conductive polymer and degradable polymer can be adjusted for controlling the conductivity and degradation rate of the mesh.

Figure 2A:
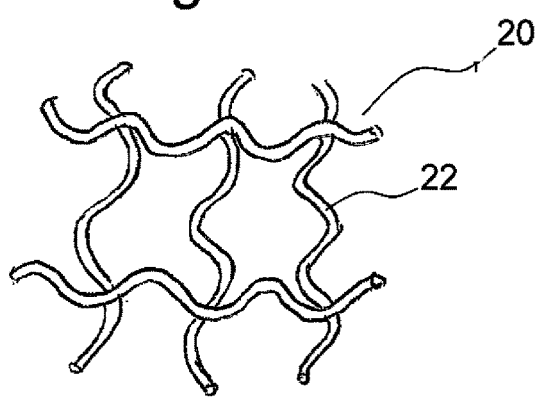
FIG. 2a is an illustration of a portion of a biodegradable conductive mesh with biodegradable monofilaments having a conductive polymeric coating.
Figure 2B:
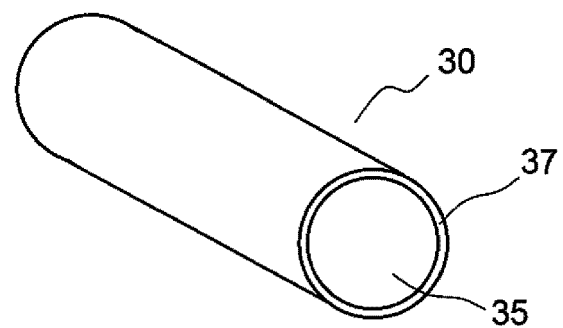
FIG. 2b is an illustration of a cross-section of a monofilament of the mesh of FIG. 2a having a conductive polymeric coating and a biodegradable polymeric core.

In another exemplary construction, as shown in FIG. 2a, the biodegradable conductive implant comprises a mesh made from at least one biodegradable fiber which is partially or entirely coated with a conductive polymer. For example, FIG. 2a shows portion of biodegradable conductive mesh implant 20 having a coated biodegradable conductive fiber 22. FIG. 2b shows a cross section of a coated biodegradable conductive fiber 22 having a core 35 that is made partially or entirely from a biodegradable polymer, or a mixture of biodegradable polymers, and a coating 37 made partially or entirely from a conductive polymer, and formed around the circumference of the fiber.

In exemplary embodiments the conductive coating on the degradable fiber has a thickness in the range of about 0.5 µm to about 25 µm, or specifically about 1 µm to about 10 µm.

In other constructions, a coated conductive fiber where the coating is present over only a part of the fiber can be used to prepare the mesh implants. For example, the coating can be present over 50% or less of the surface of the biodegradable fiber, over 25% or less, over 10% or less, or over 5% or less. For example, if partially coated, the coating can be present on one side of the implant (fibers). The coating on the fibers can be continuous so that current can be generated across the implant, from one electrode attachment point to another.

A coated mesh structure (including woven filament or molded non-woven) prepared in one of a variety of ways. Some modes of preparing involve coating a composition that includes the conductive polymer using a technique such as spraying or dipcoating.

The implant can include one or more portions where there is a greater concentration or amount of conductive polymeric material present per amount of implant material. Regions of greater concentration can be chosen based on desired areas of greater conductivity. In some aspects, the implant comprises electrode portions, for example with reference to FIG. 4, the implant 40 has a first electrode segment 51 and second electrode segment 53, that have an amount of conductive polymeric material greater per amount of implant material than in other portions of the implant.

The implant can optionally be configured so that one or more portions of the implant traverse a pelvic tissue. The one or more portions that traverse a pelvic tissue may be the first electrode position 51 and/or second electrode position 53 as referred to in FIG. 4. The traversal of tissue may be internal/internal or internal/external, and in some cases may be "transcutaneous" or "transorgan." In an exemplary case of a transcutaneous placement, the first electrode position 51 may be located external to internal pelvic tissue where most or all of the rest of the implant is placed. For example, the first electrode position 51 may be in the vagina, and the implant can extend transvaginally into an internal region of pelvic tissue, such as underneath the urethra, to provide support and treatment. A current-generating device can, in some modes of practice, be placed in contact with the first electrode position 51.

After treatment including electrical stimulation, the internally-positioned portion of the implant can degrade. Any externally-located portion of the mesh can be trimmed or removed if it does not degrade after the treatment period.

In some cases a bioactive agent can be present in the mesh. Exemplary biologically-active components include steroid hormones such as estrogen, growth factors, pro-angiogenesis factors, anti-fibrotic agents, anti-microbial agents, antibiotics, immunosuppressive agents, inhibitors of epithelial cell activation and/or migration, compounds that enhance wound regeneration, anti-inflammatory agents, anti-cancer drugs, etc. For example, the bioactive agent can comprise the ovarian steroid, estrogen or estradiol, to treat vaginal prolapse.

The biodegradable conductive mesh construct can be associated with a pelvic implant in various ways. The biodegradable conductive mesh can be a portion or all of a tissue support portion, or extension portion, or both, of a pelvic implant. Types of exemplary implants that can generally be useful for treating pelvic conditions include those previously and currently used in treating pelvic conditions, including those implants referred to as urethral "slings," "strips," "mesh strips," "hammocks," among other terms for pelvic implants.

Examples of implants for treating pelvic conditions such as incontinence or prolapse, e.g., urethral slings, can include a central support portion and one or more extension portions. An exemplary sling can generally be in the form of an implantable strip having a central support portion and two extension portions. The central support portion, extension portions, or both, can include the biodegradable conductive mesh.

In some constructions, the implant can include a tissue support portion (also referred to as a "central support portion") that can be used to support pelvic tissue such as the urethra (which includes the bladder neck), bladder, vaginal tissue, etc. The implant can also include one or more extension portion(s) that are attached to and extend from the central support portion. The one or more extension portions can lead from the support portion to or more other secondary pelvic tissue sites to hold the central support portion in a desired position for treatment. The end of an extension portion can be immobilized at the secondary pelvic tissue site to achieve this effect. For example, the end of an extension portion can be tied, sutured, adhered, or anchored to a certain pelvic tissue or anatomical structure. In some arrangements, a tissue fastener (also referred to as a "tissue anchor") can be included at an end of an extension portion, the tissue fastener being designed to attach to tissue in the pelvic region to secure the distal end of the extension portion to the tissue.

One or multiple (e.g., one, two, four, or six) extension portions can extend from a central support portion for attachment to tissue in the pelvic region, such as by extending through a tissue path to an internal attachment point (for attachment by bone anchor, tissue fastener, etc.).

Exemplary dimensions of the implant can be sufficient to allow the central support portion to contact tissue to be supported, and to allow extension portions to extend from the tissue support portion to a desired anatomical location to allow the extension portion to be secured to or pass through tissue of the pelvic region and support the tissue support portion.

The central support portion can have a desired shape and area and may be described in terms of width and length. The extension portion(s) are generally elongate, with the extension portion length being greater than the width. In some cases the central portion has a width greater than the width of the extension portion(s). In some cases the central portion has a width that is the same as the width of the extension portion(s), and here the implant can resemble a "strip" of material (e.g., mesh) with a portion of the strip near the center of the strip defining the central support portion.

Exemplary implants including the biodegradable conductive mesh can be generally shaped and sized according to previous implants for the treatment of a pelvic floor condition. For example, an implant can have features as described in the following exemplary documents: U.S. Pat. No. 7,500,945, issued Mar. 10, 2009 (Cox et al.); U.S. Pat. No. 7,070,556, issued Jul. 4, 2006, (Anderson et al.); U.S. Pat. No. 7,905,825, issued Mar. 15, 2011 (Arnal et al.); U.S. Pat. No. 7,722,528, issued May 25, 2010 (Arnal et al.); U.S. Pat. No. 7,422,557, issued Sep. 9, 2008 (Arnal et al.); U.S. Pat. No. 7,914,437, issued Mar. 29, 2011 (Gozzi et al.); United States publication number 2006/0195007, published Aug. 31, 2006 (Anderson et al.); U.S. Pat. No. 7,740,576, issued Jun. 22, 2010 (Hodroff et al.); U.S. Pat. No. 7,901,346, issued Mar. 8, 2011 (Kovac et al.); U.S. Pat. No. 7,351,197, issued Apr. 1, 2008 (Montpetit et al.); and international publication number WO/2007/016083, published Feb. 8, 2007 (Davila et al.); the entireties of each of these disclosures being incorporated herein by reference.

In some embodiments, the implant is configured for implantation into a female patient. Portions of the implant can have features to support an anatomical structure in the pelvis (i.e., a "support portion"), such as the vagina, bladder, urethra, or levator ani. The implant for female treatment can also have features, such as straps or arms that extend from a support portion of the implant, or tissue anchors or fasteners (e.g., self-fixating tips), to help maintain the implant at a desired anatomical location in the female pelvis.

For example, the implant can be used for treating urinary incontinence in a female subject, the implant including a urethral sling having a central portion and first and second ends or arms. The first and second ends/arms are coupled to and extend from the central support portion. Following implantation, the arms are used to help secure or position the implant at a desired anatomical location in the pelvis.

The pelvic implants with the biodegradable conductive mesh can be electrically connected to a current-generating device. The current-generating device can be one that is implanted in the body, or one that remains external to the body. If the current-generating device is implantable it can include a battery and an electric control unit to modulate the current generated by the battery. If the current-generating device is to remain external, it can include a battery or can be configured to be connected to a secondary power supply, or both. The current-generating device, whether implantable or configured to be external, can include features to modulate the current generated by the battery. The control unit can deliver direct current or alternating current. The control unit can optionally include a pulse-generator to generate a periodic electric current across the biodegradable conductive mesh.

The current-generating device can be connected to the biodegradable conductive mesh via electrical leads. If the current-generating device is external to the body, in some embodiments the leads can pass through an incision in the skin and to desired portions on the mesh. In this manner, the leads of the system can be configured for "transcutaneous" use. If the current-generating device is implanted the leads can pass through tissue or a portion(s) of the body to desired portions on the mesh. An implanted current-generating device can be placed in a portion of the body where it can be readily removed during or after degradation of the mesh. In other modes of practice, the leads of the system can be configured for "transorgan" use, such as when the leads traverse tissue defining a particular organ in the pelvic anatomy.

Electrical leads can be connected to desired portions of the implant. For example, a first lead (e.g., positive) is connected to a first position on the implant, and a second lead (e.g., negative) is connected to a second position on the implant. The portion of the implant between the first and second positions includes biodegradable conductive mesh, and, as such, current can flow between the first and second positions, and an electric field can be generated in the corresponding area of pelvic tissue. The first and second positions on the implant can be chosen based on the surgical placement of the implant, and the desired area of tissue intended to be stimulated by the electrical field.

Figure 3:
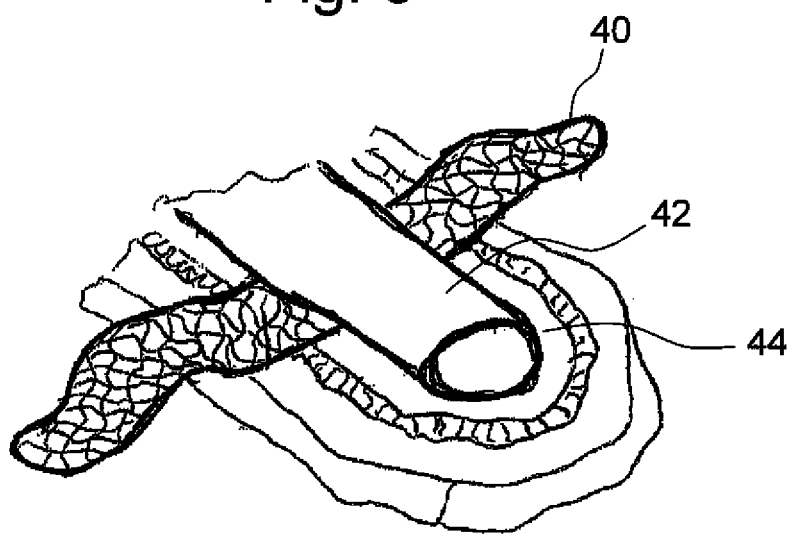
FIG. 3 is an illustration of a pelvic tissue area with a biodegradable conductive mesh implant supporting a tubular organ.
Figure 4:
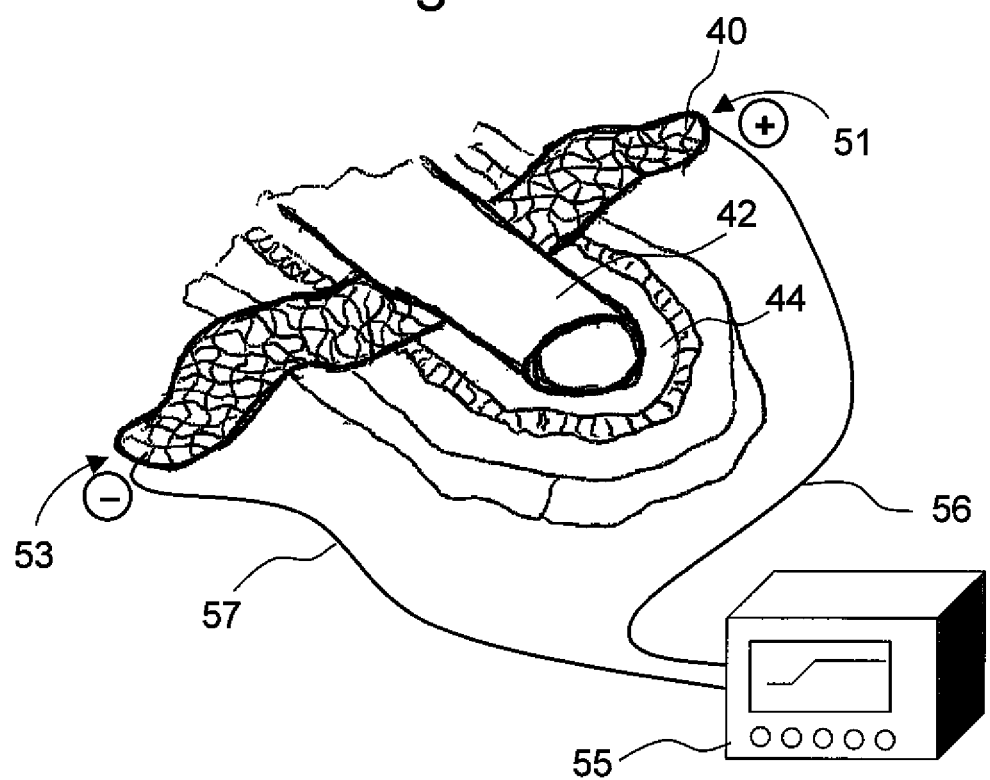
FIG. 4 is an illustration of a pelvic tissue area with a biodegradable conductive mesh implant connected to a current generator.

In some modes of practice the implant is placed in association with, such as underneath, a tissue to be supported. For example, with reference to FIG. 3, an implant 40 including the biodegradable conductive mesh is placed under a tubular organ 42, such as the urethra or portion of the bladder. Tissue 44 in association with or supporting the tubular organ 42 can be affected by an electrical field generated by the biodegradable conductive mesh. With reference to FIG. 4, the implant 40 is connected to the distal end of a first lead 56 (positive) at a first electrode position 51, at one end on the implant. The distal end of the second lead 56 (negative) is connected to a second electrode position 53, at the other end of the implant. The proximal ends of leads 56 and 57 are connected to current-generating device 55, which can be implanted in the body, or can be external to the body.

After implantation, the current-generating device 55 is activated to deliver current across the implant, which generates an electric field in the pelvic tissue area affecting the tissue 44 that is in association with and/or supporting the tubular organ 42. For example, a DC current can be safely applied to the implant shortly after surgical placement. In some modes of practice, current can be delivered to the biodegradable conductive mesh, for example, using a DC current of 50-100 mV. The current can be delivered for a predetermined amount of time either. Preferably the current is supplied intermittently, such as in short pulses. In some cases, the electrical stimulation may be applied transcutaneously at the sites where the mesh ends can be electrically reached.

The therapeutic electric field around the implant and surrounding tissues facilitates the healing of the wound between the mesh material and surrounding tissues through one or more physiological mechanisms selected from electrotaxis, cytokine secretion, mitochondrial function, cellular adhesion, spreading and proliferation. The electrical stimulation can encourage healthy tissue growth into the mesh and enhance healing. As a result, tissue attachment to the mesh is strengthened, with a better outcome of mesh mechanical support.

Figure 5:
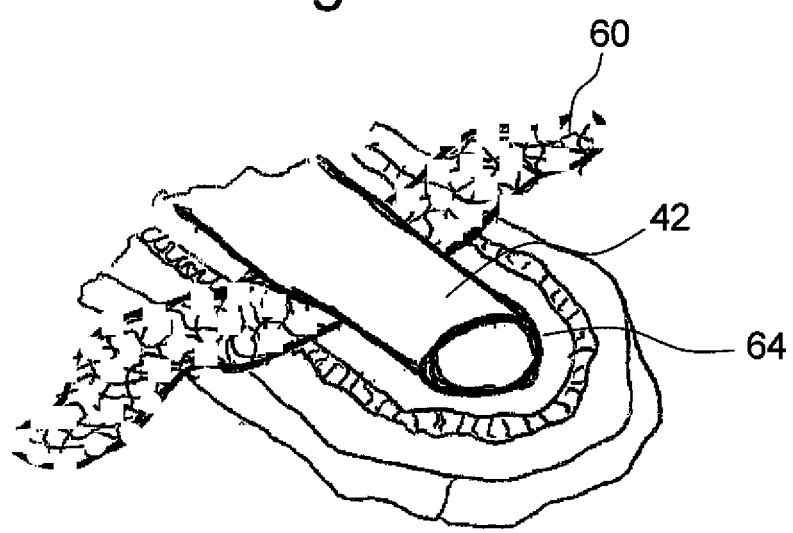
FIG. 5 is an illustration of a pelvic tissue area with degraded portions of the implant following a period of degradation.

After a period of time following implantation, electrical stimulation, and an improved tissue response as promoted by the presence of the electrical field, the mesh begins to degrade. The rate of degradation can coincide with the establishment and reconfiguration of supporting pelvic tissues in vivo. In other words, the mechanical support originally provided by the mechanical structure of the mesh is replaced by the new tissue growth in association with the mesh, and the mesh is destined to degrade and be absorbed in vivo. FIG. 5 shows the pelvic implant area with partially degraded portions of the mesh, which subsequently can become fully degraded with the degradation materials absorbed by the body. The pelvic tissue 64 affected by the electrical field and previously in association with the implant is healed and strengthened, and capable of properly supporting the tubular organ 42 to treat the condition, such as incontinence.

Implants of the invention can be part of a system or kit. The system or kit can include components for carrying out procedures for the insertion of the implant in a patient, and its use following implantation.

As described herein, a current-generating device and leads can be used following placement of the implant. These current-generating device and leads, as well as any other component useful for the current-generating feature of the implant, can be included in the system or kit.

The system of kit can also include components useful for a surgical process of introducing and securing the implant in the body. Exemplary components can include tissue fasteners, tools for introducing the implant into a patient using a surgical insertion procedure, scalpels or knives for making the incision, and needles and suture material for closing the incision. All or parts of the kit can be sterilely packaged. Insertion tools useful for insertion of the implant can include a handle and an elongate needle, wire, or rod extending from the handle. The needle, wire, or rod can be shaped (such as helical, straight, or curved) to be useful to carry the implant through a desired tissue path in the pelvic region.

What is claimed is:

1. A medical device:
   a mesh implant having a plurality of biodegradable conductive fibers, the plurality of biodegradable conductive fibers including a first type filament and a second type filament, the first type filament being a conductive polymer and the second type filament being a mixture of a coated biodegradable conductive fiber including a core constructed from a biodegradable polymer and a conductive coating constructed from an electrically conductive polymer, the conductive coating covering less than 50% of an outer surface of the core,
   the mesh implant having a first end portion including a first end and a second end portion including a second end, the mesh implant including a first portion, a second portion, and a third portion, the first portion being disposed on the first end portion and defining a first electrode segment having first coated biodegradable conductive fiber portions, the second portion being disposed on the second end portion and defining a second electrode segment having second coated biodegradable conductive fiber portions, the third portion being disposed between the first end portion and the second end portion and having third coated biodegradable conductive fiber portions, the first electrode segment and the second electrode segment having greater concentrations of the conductive polymer than the third portion of the mesh implant;
   a first lead configured to be coupled to the first electrode segment; and
   a second lead configured to be coupled to the second electrode segment.

2. The medical device of claim 1, wherein the biodegradable polymer is selected from the group consisting of polyesters, polyhydroxyalkanoates, polyorthoesters, polyalkeneanhydrides, and polyanhydrides.

3. The medical device of claim 1, wherein the coated biodegradable conductive fiber is in the form of a monofilament.

4. The medical device of claim 1, wherein the conductive coating has a thickness in a range of about 0.5 μm to about 25 μm.

5. The medical device of claim 1, wherein the mesh implant includes a woven structure.

6. The medical device of claim 1, wherein the conductive coating has a thickness in a range of about 1 μm to about 10 μm.

7. The medical device of claim 1, wherein the conductive coating includes a concentration of polyaniline in a range of 0.5 to about 10%.

8. The medical device of claim 1, wherein the electrically conductive polymer is selected from the group consisting of polyaniline, polypyrrole and polythiophene.

9. The medical device of claim 1, wherein the electrically conductive polymer comprises polypyrrole.

10. The medical device of claim 1, wherein the electrically conductive polymer comprises polyaniline.

11. The medical device of claim 1, wherein the electrically conductive polymer covers less than 10% of the outer surface of the core.

12. The medical device of claim 1, wherein the electrically conductive polymer covers less than 5% of the outer surface of the core.

13. The medical device of claim 1, wherein the electrically conductive polymer covers only one side of the outer surface of the core.

14. The medical device of claim 13, wherein the covered electrically conductive polymer is continuous from one electrode attachment to another electrode attachment point.

15. A system comprising:
    a mesh implant configured for placement at a pelvic floor tissue, the mesh implant including a plurality of biodegradable conductive fibers, the plurality of biodegradable conductive fibers including a first type filament and a second type filament, the first type filament being a conductive polymer and the second type filament being a mixture of a coated biodegradable conductive fiber including a core constructed from a biodegradable polymer and a conductive coating constructed from an electrically conductive polymer, the electrically conductive polymer being disposed around an outer surface of the core,
    the mesh implant having a first end portion including a first end and a second end portion including a second end, the mesh implant including a first portion, a second portion, and a third portion, the first portion being disposed on the first end portion and defining a first electrode segment having first coated biodegradable conductive fiber portions, the second portion being disposed on the second end portion and defining a second electrode segment having second coated biodegradable conductive fiber portions, the third portion being disposed between the first end portion and the second end portion and having third coated biodegradable conductive fiber portions, the first electrode segment and the second electrode segment having greater concentrations of the conductive polymer than the third portion of the mesh implant;
    a first lead configured to be coupled to the first electrode segment;

a second lead configured to be coupled to the second electrode segment; and an electrical stimulator unit coupled to the first lead and the second lead, the electrical stimulator unit configured to generate a current through the mesh implant.

16. The system of claim 15, wherein the monofilament includes at least one groove along a length of the monofilament.

17. A method for treating pelvic floor tissues, the method comprising:
(a) placing a mesh implant at a pelvic floor tissue, the mesh implant including a plurality of biodegradable conductive fibers, the plurality of biodegradable conductive fibers including a first type filament and a second type filament, the first type filament being a conductive polymer and the second type filament being a mixture of a coated biodegradable conductive fiber including a core constructed from a biodegradable polymer and a conductive coating constructed from an electrically conductive polymer, the conductive coating covering less than 50% of an outer surface of the core, the mesh implant having a first end portion and a second end portion, the mesh implant consisting of a first portion, a second portion, and a third portion, the first portion being disposed on the first end portion and defining a first electrode segment having first coated biodegradable conductive fiber portions, the second portion being disposed on the second end portion and defining a second electrode segment having second coated biodegradable conductive fiber portions, the third portion being disposed between the first end portion and the second end portion and having third coated biodegradable conductive fiber portions, the first electrode segment and the second electrode segment having greater concentrations of the conductive polymer than the third portion of the mesh implant, wherein a first lead is coupled to the first electrode segment, and a second lead is coupled to the second electrode segment;
(b) generating a current through the mesh implant to promote a tissue healing response; and
(c) allowing the mesh implant to degrade at the site of placement.

* * * * *